United States Patent
Desjonqueres

(10) Patent No.: US 6,416,767 B1
(45) Date of Patent: Jul. 9, 2002

(54) USE OF PEROXIDIZED LIPIDS AS AGENTS INTENDED TO PREVENT AND/OR TO TREAT THE IRRITANT EFFECTS OF AN ACTIVE PRINCIPLE

(75) Inventor: Stéphane Desjonqueres, Maisons Laffitte (FR)

(73) Assignee: Laboratoires Carilene, Montesson (FR)

( * ) Notice: Subject to any disclaimer, the term of this patent is extended or adjusted under 35 U.S.C. 154(b) by 0 days.

(21) Appl. No.: 09/333,924

(22) Filed: Jun. 16, 1999

(30) Foreign Application Priority Data

May 12, 1999 (FR) .............................. 99 06079

(51) Int. Cl.⁷ .................................. A61K 7/00
(52) U.S. Cl. ................ 424/401; 424/450; 514/844; 514/938
(58) Field of Search ................ 424/401, 450; 514/844, 938

(56) References Cited

FOREIGN PATENT DOCUMENTS

| EP | 0225831 | 6/1987 |
|----|---------|--------|
| EP | 0391780 | 10/1990 |
| EP | 0465313 | 1/1992 |
| EP | 0481148 | 4/1992 |
| FR | 2750331 | 1/1998 |
| FR | 2753374 | 3/1998 |
| WO | 97/26892 | 7/1997 |

*Primary Examiner*—Sabiha Qazi
*Assistant Examiner*—Michael A. Williamson
(74) *Attorney, Agent, or Firm*—Dennison, Scheiner & Schultz

(57) ABSTRACT

A composition for topical application to the skin, contains an active principle with irritant character in a cosmetically or pharmaceutically acceptable vehicle, in which the vehicle contains more than 5% by weight of peroxidized vegetable oil having a peroxidation level of between 5 and 600 milliequivalents per kg. The presence of the peroxidized oil reduces the irritant character of the principle, particularly capsaicin and retinoic acid.

23 Claims, No Drawings

USE OF PEROXIDIZED LIPIDS AS AGENTS INTENDED TO PREVENT AND/OR TO TREAT THE IRRITANT EFFECTS OF AN ACTIVE PRINCIPLE

BACKGROUND OF THE INVENTION

The present invention relates to a novel use of peroxidized lipids as agents intended to prevent and/or to treat the irritant effects of an active principle.

More specifically, the invention relates to a composition for topical application to the skin for treating or preventing irritation due to the irritant nature of an active principle comprised in said composition and to a method of treating of human body intended to treat or prevent the irritant effect of an active principle.

It is well known that a certain number of active principles intended to be used topically on the skin, especially active principles used in dermatology, are capable of generating severe or even very severe tolerance problems. The secondary effects of these active principles can range from simple irritation up to manifestations of eczematous type, risks of blisters or vesicles on the skin.

An example of a well-known product causing such effects is capsaicin which corresponds to the formula:

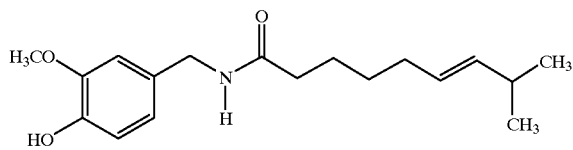

It is a product which is well known for its vasodilatory action. Owing to this action, capsaicin is widely used in preparations for local use whose effect is to obtain an influx of blood and a sensation of heat. To this end, capsaicin is very particularly indicated in the treatment of pain in rheumatology. However, one of the disadvantages of this product is that it is an irritant product which causes smarting of the skin.

Another example of a product also known for its particularly irritant character is constituted by retinoic acid, alternatively called vitamin A acid, the active principle particularly used in topical compositions intended for the treatment of acne and of wrinkles.

Finally, other active principles are also well known for their irritant character. Mention may be made, in particular, of synthetic retinoids, 5-fluoro-uracil, benzoyl peroxide as well as nicotinamide and salicylic acid.

Various peroxidized lipids, especially obtained by peroxidation of natural vegetable oil, are known. Mention may be made, in particular, of the following patents BSM No. 2 330 M, EP-A-293 535, FR-A-2 591 112, EP-A-225 831, EP-A-225 832, EP-A-225 833, EP-A-226 506, FR-A-2 461 744, FR-A-2 539 142 and EP-A-117 962, which concern either the preparation of such peroxidized lipids or their application in various fields, in particular in the treatment of certain conditions in the field of rheumatology or of traumatology, or alternatively as a cicatrizing product.

European Application EP-A-0 481 148 describes pharmaceutical compositions, and especially pharmaceutical compositions from the tumor therapy field, containing, as active principles, a hyperoxygenated oil and an oxygenated derivative of retinene, in combination with a vehicle or a non-irritant pharmaceutically compatible inert excipient. In these compositions, the hyperoxygenated oil is used at doses of always less than 5% by weight and their aim is to promote the passage of the retinene derivative into the dermis and its attachment to the lesions to be treated.

SUMMARY OF THE INVENTION

It has now quite surprisingly been discovered that it was possible to considerably decrease the irritant character of an active principle, especially of a pharmaceutical active principle, in particular of a dermatological active principle, for topical application by simultaneously applying to the skin a sufficiently large quantity of a composition containing a sufficiently large quantity of peroxidized lipids.

Thus, the present invention relates to a novel use of peroxidized lipids, in particular of peroxidized oils, as agents intended to prevent and/or to treat the irritant effects of an active principle.

According to a particularly advantageous aspect, the invention relates to compositions, especially pharmaceutical compositions, containing at one and the same time the irritant active principle and a sufficient quantity of peroxidized lipids.

Thus, for example, according to a first aspect, the invention relates to novel compositions for topical application to the skin, containing an active principle, especially a pharmaceutical active principle, with irritant character in a cosmetically or pharmaceutically acceptable vehicle containing more than 5% by weight of peroxidized lipids.

Given the severe character of irritation phenomena which the present invention proposes to resolve, the compositions aimed at by the present invention are generally compositions from the pharmaceutical field, in particular from the dermatological field.

DETAILED DESCRIPTION OF THE INVENTION

The peroxidized lipids whose use is claimed according to the present invention result from the peroxidation of unsaturated fatty substances.

The degree of peroxidation is measured according to the standard ISO 3960.

To carry out the present invention, peroxidized lipids having a peroxidation level of between 5 and 600 milliequivalents per kilo, preferably between 30 and 500 milliequivalents per kilo, may advantageously be chosen.

This peroxidation level may more advantageously be between 50 and 300 milliequivalents per kilo, more preferably between 50 and 150 milliequivalents per kilo.

The preferred peroxidized lipids used according to the invention result from the peroxidation of lipids of vegetable origin, preferably of lipids from a natural vegetable oil.

Examples of natural oil chosen according to the invention which may be mentioned are sweet almond oil, hazelnut oil, peanut oil, corn oil, grapeseed oil, sesame oil and safflower oil. It is also possible to use a mixture of these oils.

According to a particularly preferred variant of the invention, peroxidized corn oil and very particularly a corn oil having a level of peroxidation of between 5 and 600 milliequivalents per kilo may be chosen.

The peroxidized lipids used according to the invention are advantageously formed of major constituents, generally representing at least 80% of the triglyceride mass, corresponding to the formula

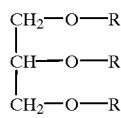

in which the radicals R are mainly represented by partially peroxidized $C_{18}$ unsaturated acids (as a function of the level of peroxidation of said lipid).

The compositions of the invention can be in any form compatible with topical application to the surface of the skin. These compositions may preferably be found in the form of an oil-in-water or water-in-oil type emulsion, a cream, a lotion, a milk or a gel, in particular an oily gel based on colloidal silica.

The compositions of the invention contain, for the effect of the peroxidized lipid to be perceptible and to allow the irritant effect of the active principle to be prevented or treated effectively, more than 5% by weight of this peroxidized lipid.

According to an advantageous variant of the invention, the concentration of peroxidized lipids in the composition is between 5 (excluded value) and 97% by weight, preferably between 10 and 95%.

The peroxidized lipids concentration of the compositions of the invention depends, at the same time, on the nature of the active principle with irritant character and on its degree of aggressiveness with respect to the skin. It thus depends at the same time on the concentration and the nature of the active principle. However, it is clear that for the same active principle, this concentration will be all the higher because the concentration of the active principle in the composition will itself be higher.

In addition, and this forms an additional advantage of the composition according to the invention, the presence in the said composition of peroxidized lipids in sufficient quantity allows, if necessary, the customary concentrations of active principle to be perceptibly increased, without having additional risks of irritation.

As set out above, the invention is especially directed at the irritant active principles of compositions known in the pharmaceutical field, especially in the dermatological field.

By way of particularly irritant active principle for which the present invention provides a particularly effective solution, mention may be made of capsaicin, synthetic retinoids, retinoic acid, benzoyl peroxide, nicotinamide, salicylic acid, hydroquinone and 5-fluorouracil.

As is evident in particular from the examples which follow, the invention turns out to be very particularly effective in the case of capsaicin.

According to a particularly advantageous variant of the invention, in the case of capsaicin the composition is in the form of an emulsion of water-in-oil or oil-in-water type containing more than 5 and at the most 50% by weight of peroxidized oil and from 0.010% to 0.080% of pure capsaicin.

According to another variant of the invention and, still in the case of capsaicin, the compositions of the invention may be in the form of an oily gel, especially of a gel based on colloidal silica, and in this case advantageously contain from 40 to 97% by weight of peroxidized oil and from 0.010% to 0.08% of pure capsaicin.

Another active principle for which the invention provides a particularly advantageous solution for avoiding its skin-irritant character is retinoic acid.

In the case of retinoic acid, the composition is advantageously in the form of an emulsion containing, by weight, preferably from 0.010% to 0.07% of pure retinoic acid. The concentration of peroxidized oil of these compositions is greater than 5% by weight and, preferably, between 7% and 90%, preferably between 10 and 50%.

Still in the case of retinoic acid, it is also possible for the compositions to be in gel form, in particular in the form of gels containing from 0.010% to 0.07% by weight of pure retinoic acid per 40 to 97% of peroxidized oil.

Of course, it is additionally possible for the compositions of the invention to comprise different additives conventionally used in this type of composition for topical use, in particular in dermatology.

Thus, for example, it is possible for the compositions of the invention to additionally contain emulsifying agents, perfumes and preservatives of the type conventionally used in compositions for topical use in dermatology.

As set out above, the invention provides a particularly effective means of preventing or treating all the intolerance phenomena connected with the use of pharmaceutical, especially dermatological, products, known for their irritant or very irritant characteristics, the peroxidizing oils acting with an anti-erythematous or anti-reactive action, especially allowing any eczematous reaction as well as any risk of formation of blisters or of vesicles on the surface of the skin to be avoided during the application of an active principle known for its particularly irritant character.

The invention thus offers a means of effectively combating such reactions by applying to the skin, simultaneously, peroxidized oil in sufficient quantity and the active principle, with a view to avoiding the unpleasant symptoms connected with the aggressiveness of this active principle.

The invention thus covers any of the procedures for topical treatment of the skin in which an active principle whose irritant character is known and a sufficient quantity of peroxidized oil are applied simultaneously to avoid all the unpleasant symptoms connected with the application of this active principle to the skin.

Thus, according to a second aspect, the invention relates to a method of preventing irritation due to an active principle applied to a part of the human body, comprising the application to the same part of the body of an effective amount of peroxidized lipids.

According to a first embodiment of the above method, the active principle and the peroxidized lipids are included in the same composition which is a composition as defined above.

According to another embodiment of the invention, the active principle and the composition comprising the peroxidized lipids may be applied separately.

In both cases, the method allows eczematous manifestations, formations of blisters or of vesicles as well as any erythematous action connected with the topical application to the skin of said active principle to be prevented and/or avoided.

As set out above, it is possible to obtain this effect by applying to the skin a composition such as defined above containing the peroxidized oil and the active principle for which it is wished to prevent the irritant effect.

It is also possible to obtain this effect by applying to the skin, conjointly with a composition containing an irritant active principle, a composition containing more than 5% by weight of peroxidized lipids such as defined above.

The compositions which can be used for carrying out this treatment procedure, containing or not containing the active principle for which it is wished to avoid the secondary effects, can be in one of the forms defined above, in particular in gel or emulsion form and can contain different additives conventionally used in the field of dermatology.

The examples which follow are given as purely illustrative of the present invention.

EXAMPLES

Example 1

Demonstration of the Effect of Peroxidized Oils on the Tolerance of Capsaicin

The object of the study carried out according to this example is to compare the cutaneous tolerance of a product according to the invention with that of a product which is identical in every respect but in which the peroxidized oil has been replaced by paraffin oil.

This comparative study was carried out by proceeding according to a first so-called "pilot" test and a second so-called "dermatological" test over a period of greater than 4 days, carried out under dermatological control.

The protocols of the two tests are given below.

1) Protocol of the Tests Used a) Protocol of the "Pilot" Study

Inclusion Criteria

Adult men or women in good health

Exclusion Criteria

Any dermatosis

Any intolerance to peroxygenated oils

Application Method

The experimenter himself applies a knob of the product 1 to the left lateral lower half of the neck of the volunteer to the junction with the shoulder. The experimenter firmly massages from the ear to the shoulder for at least 10 to 25 s until absorption of the product 1 by the skin is complete.

The experimenter then washes his hands and then he applies a knob of the product 2 to the right lateral lower half of the neck of the volunteer to the junction with the shoulder. The experimenter then firmly massages from the ear to the shoulder for at least 10 to 25 s until the absorption of the product 2 by the skin is complete.

After 5 min, the volunteer fills in a first part of the comment slip which is given to him by precisely stating the level of the possible stinging effect of the product felt as well as the level of the sensation of heat possibly felt.

For each of these effects, the volunteer has the choice between 4 levels: none, very slight, obvious, severe.

The experimenter, for his part, fills in the second part of the comment slip relating to the possible appearance and to the intensity of erythema by classifying the level in the same manner (none, very slight, obvious, severe).

b) Protocol of the "Dermatological" Test

A second so-called "dermatological" test was carried out on the same basis but with a longer period of 4 days (from D1 to D4) with 3 applications per day.

More precisely, in this test the products are applied three times per day on the side of the neck concerned in the following manner: application of one knob of product to the lateral lower half of the neck to the junction with the shoulder and massage for 20 to 25 seconds until the product has penetrated the lateral part of the neck, by starting from the ear to the junction of the neck with the shoulder.

No other product must be applied to the neck except for toilet products.

On D1

The volunteers come to the laboratory, they are informed of the study procedure and fill in a consent slip and an information slip in duplicate.

A clinical examination is carried out on the two sides of the neck under dermatological control.

Application of the two products (one on each lateral face of the neck) by the technician.

5 minutes after the end of the application, the technician questions the volunteers about the sensations which they perceive.

These sensations are evaluated according to the following scale:

0: nil

1: very slight

2: slight

3: moderate

4: severe

5: very severe

Distribution of the products which the volunteers apply at home according to the same prococol.

The volunteers make two other applications during the day and fill in two evaluation slips 5 minutes after application (washing the hands between each application to each neck half).

On D2 and on D3

Three applications during the day of each product according to the same protocol.

5 minutes after the end of each application, the volunteers fill in the evaluation slips.

On D4

The volunteers come to the laboratory and return the products and the evaluation slips.

Last application by the technician.

5 minutes after the end of the application, the technician questions them on the sensations which they perceive.

2) Products Tested

The products tested in this example according to the two protocols above have the composition given in the two tables below:

Product 1:gel with 0.075% by weight of pure capsaicin in the presence of liquid paraffin oil (comparative), Product 2:gel with 0.075% by weight of pure capsaicin in the presence of deodorized peroxidized corn oil (example according to the invention).

TABLE 1

(Product 1)

| RAW MATERIALS | % by weight | Quantities weighed for 3000 g (g) |
| --- | --- | --- |
| Petroleum jelly | 91.925 | 2535 |
| Aérosil ® 300 | 7 | 210 |
| Pronalen capsicum with 1% of capsaicin or in pure capsaicin on the finished product | 0.075 | 225 |
| Perfume | 1 | 30 |

TABLE 2

(Product 2)

| RAW MATERIALS | % by weight | Quantities weighed for 3000 g (g) |
| --- | --- | --- |
| Deodorized peroxidized corn oil | 90.925 | 2505 |
| Aérosil ® 300 | 7 | 210 |
| Pronalen capsicum with 1% of capsaicin or in pure capsaicin on the finished product | 0.075 | 225 |
| Perfume | 2 | 60 |

3) Results
a) Pilot Test

The "pilot" test was carried out on 16 persons according to the protocol given above.

Tables 3, 4 and 5 below respectively give the levels obtained as far as the stinging effect is concerned, the sensation of heat and the level of erythema for the product according to the invention (product 2) in comparison with product 1 containing petroleum jelly in replacement of the peroxidized oil.

TABLE 3

| | Stinging effect | | | | |
|---|---|---|---|---|---|
| | None | Very slight | Obvious | Severe | TOTAL |
| Product 1 | 0 | 1 | 12 | 3 | 16 |
| Product 2 | 14 | 2 | 0 | 0 | 16 |

TABLE 4

| | Sensation of heat | | | | |
|---|---|---|---|---|---|
| | None | Very slight | Obvious | Severe | TOTAL |
| Product 1 | 7 | 9 | 0 | 0 | 16 |
| Product 2 | 15 | 1 | 0 | 0 | 16 |

TABLE 5

| | Erythema | | | | |
|---|---|---|---|---|---|
| | None | Very slight | Obvious | Severe | TOTAL |
| Product 1 | 4 | 3 | 7 | 2 | 16 |
| Product 2 | 15 | 1 | 0 | 0 | 16 |

It clearly appears that the peroxidized oils allow the secondary effects of capsaicin to be decreased much more distinctly than vaseline.

b)

The "dermatological" test was applied to 40 healthy volunteers, one of masculine sex and 39 of feminine sex, of age between 18 and 57 years (average age 33±2 years) who have participated in this study.

This test was followed by a statistical working of the results and allowed the results observed in the "pilot" test to be confirmed in every point. More precisely:

on each application, the smarting felt with product 1 is distinctly greater than that felt with product 2, in the same way the erythemas noted are distinctly more significant with product 1 than with product 2.

The sensation of heat is likewise distinctly greater with product 1 and the itching was more often greater with product 1.

Thus, for example, for all the parameters studied, product 1 gave distinctly more intense sensations than product 2. This second test thus allowed the results of the pilot test to be confirmed.

Example 2

Demonstration of the Effect of the Presence of a Peroxidized Oil on Tolerance of Retinoic Acid a) Test Protocol The method used according to this test is that described by PHILLIPS et al. in Toxic and Applied Pharmacology, 21: 369–382, 1972.

According to this method, the products to be tested are incorporated into patches.

The patches are renewed daily, 5 days per week, for 21 days at the same place on the skin.

At the end of the test, a reading of the irritant character of the product is carried out by allocating a mark of between 0 and 4 according to the scale below:

0=no effect
0.5=doubtful reaction
1=erythema
2=erythema and induration
3=erythema and induration and vesicles
4=blisters b) Products Tested 4 products were compared as part of the study and each was applied under the same conditions to the individuals participating in this study.

They are:

Product No.1: a gel containing, by weight, 90% of peroxidized oil and 0.05% of retinoic acid Product No. 2: the product marketed by Laboratoires ORTHO under the brand RETIN-A-® Micro with 0.1% of retinoic acid Product No. 3: the product marketed by Laboratoires ORTHO under the brand RETIN-A-® Gel with 0.025% of retinoic acid Product No. 4: the product marketed by Laboratoires ORTHO under the brand RETIN-A-® Gel with 0.01% of retinoic acid c) Results Obtained The test was carried out, according to the protocol above, on 25 subjects of more than 18 years and in good health.

The cumulative results (sum of marks allocated, for each product, by the 25 subjects participating in the study), observed at the end of 21 days according to the reading scale given above, were the following:

Product 1:0
Product 2:15
Product 3:80
Product 4:54

This study thus clearly shows that, under the conditions of the test, the product according to the invention turns out to be much less irritating than the comparative products.

Example 3

Formulation Bases Which Can Be Used as a Vehicle For the Compositions of the Invention The proportions in the examples which follow are given in percentage by weight.

a) Oily liquid preparation

| | |
|---|---|
| Peroxidized vegetable oil | 45% |
| Liquid paraffin oil | 34.1% |
| Propyl parahydroxybenzoate | 0.2% |
| Stearin | 8% |
| Silicone oil | 10.7% |
| Perfume | 2% | b) Oily lotion

| | |
|---|---|
| Peroxidized vegetable oil | 36% |
| Hazelnut oil | 60% |
| Perfume | 4% |

-continued

| c) | Aqueous-alcoholic lotion | |
|---|---|---|
| | Peroxidized vegetable oil | 10% |
| | Dragoxate-2-ethylethyl-2-ethyl hexanoate | 3% |
| | Butylhydroxyanisole | 0.01% |
| | Denatured alcohol 99.9 | 23% |
| | Perfume | 0.10% |
| | Demineralized water | QSP 100 |
| d) | Water-in-oil emulsion | |
| | Peroxidized vegetable oil | 30% |
| | Semi-synthetic glycerides | 30% |
| | Water | QSP 100 |
| e) | Cream containing an emulsion of oil-in-water type | |
| | Peroxidized vegetable oil | 20% |
| | Anionic acrylic copolymers in dispersion in white oil | 4.00% |
| | Sodium methyl parahydroxybenzoate | 0.15% |
| | Sodium propyl parahydroxybenzoate | 0.05% |
| | Methylchloroisothiazoline-methylisothiazolinone | 0.0012% |
| | Perfume | 0.05% |
| | Demineralized water | QSP 100 |
| f) | Aqueous gel | |
| | Uvinul MS 40 (Laserson) | 0.050% |
| | Triethanolamine 99 | 0.5% |
| | Carbopol 934 2% solution | 25% |
| | Peroxidized vegetable oil | 10% |
| | Denatured ethyl alcohol 95/96% | 40% |
| | Perfume | 0.30% |
| | Demineralized water | QSP 100 |
| g) | Cream containing an emulsion of oil-in-water type | |
| | Peroxidized vegetable oil | 25% |
| | Salcare SC 81 | 6% |
| | Perfume | 1% |
| | Triethanolamine | 0.85% |
| | Methyl para-hydroxybenzoate | 0.15% |
| | Propyl para-hydroxybenzoate | 0.05% |
| | Chloromethylchloroisothiazoline, chloromethylisothiazolinone | 0.05% |
| | Demineralized water | QSP 100 |
| h) | Oily gel | |
| | Peroxidized vegetable oil | 92.20% |
| | Aerosil 300 | 7% |
| | Aroma; perfume | 0.8% |

What is claimed:

1. A composition for topical application to the skin, containing an effective amount of capsaicin in a cosmetically or pharmaceutically acceptable vehicle, wherein said vehicle contains more than 5% by weight of peroxidized vegetable oil having a peroxidation level of between 5 and 600 milliequivalents per kg.

2. A composition according to claim 1, wherein said peroxidized vegetable oil consists essentially of partially oxidized triglycerides corresponding to the general formula:

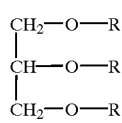

in which the radicals R are partially peroxidized $C_{18}$ unsaturated acids.

3. A composition according to claim 1, wherein said peroxidized vegetable oil is obtained from a natural vegetable oil.

4. A composition according to claim 3, wherein said natural vegetable oil is selected from the group consisting in sweet almond oil, hazelnut oil, peanut oil, corn oil, grapeseed oil, sesame oil, safflower oil and mixtures thereof.

5. A composition according to claim 1, which is in the form of an oil-in-water emulsion, a water-in-oil emulsion, a cream, a lotion, a milk or gel.

6. a composition according to claim 1, wherein the capsaicin is an active principle.

7. A composition according to claim 6, which is in the form of a water-in-oil emulsion or an oil-in-water emulsion containing more than 5% and at most 50% by weight of peroxidized oil and from 0.010% to 0.080% of pure capsaicin.

8. A composition according to claim 6, which is in the form of an oily gel and contains from 40 to 97% by weight of peroxidized oil and from 0.010% to 0.08% of pure capsaicin.

9. A composition according to claim 1, wherein the capsaicin is present in an amount of 0.010 to 0.080% by weight and the peroxidized oil is present in an amount of 40 to 97% by weight.

10. A composition for tropical application to the skin, containing 0.010 to 0.07% by weight retinoic acid, in a cosmetically or pharmaceutically acceptable vehicle, wherein said vehicle contains 40 to 97% by weight of peroxidized vegetable oil having a peroxidation level of between 5 and 600 milliequivalents per kg.

11. A composition according to claim 10, wherein said peroxidized vegetable oil consists essentially of partially oxidized triglycerides corresponding to the general formula:

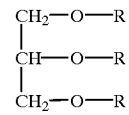

in which the radicals R are partially peroxidized $C_{18}$ unsaturated acids.

12. A composition according to claim 10, wherein said peroxidized vegetable oil is obtained from a natural vegetable oil.

13. A composition according to claim 12, wherein said natural vegetable oil is selected from the group consisting of sweet almond oil, hazelnut oil, peanut oil, corn oil, grapeseed oil, sesame oil, safflower oil, and mixtures thereof.

14. A composition according to claim 10, in the form of a gel.

15. A method of treating the skin for preventing or treating irritation due to application of an effective amount of capsaicin as an active principle, comprising the application of an effective amount of a composition containing more than 5% by weight of peroxidized vegetable oil having a peroxidation level of between 5 and 600 milliequivalents per kg, said active principle being included in said composition or applied conjointly with said composition, the peroxidized vegetable oil being present in an amount sufficient to reduce the irritant character of the active principle.

16. A method according to claim 15, wherein said peroxidized vegetable oil consist essentially of partially oxidized triglycerides corresponding to the general formula:

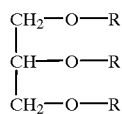

in which the radicals R are partially peroxidized $C_{18}$ unsaturated acids.

17. A method according to claim 15, wherein said peroxidized vegetable oil is obtained from a natural vegetable oil.

18. A method according to claim 12, wherein said natural vegetable oil is selected from the group consisting of sweet almond oil, hazelnut oil, peanut oil, corn oil, grape seed oil, sesame oil, safflower oil and mixtures thereof.

19. A method according to claim 15, wherein aid composition is in the form of an oil-in-water emulsion, a water-in-oil emulsion, a cream, a lotion, a milk or a gel.

20. A method according to claim 15, wherein said composition is in the form of a water-in-oil or an oil-in-water emulsion containing more than 5% and at most 50% by weight of peroxidized oil and from 0.010% to 0.080% by weight of pure capsaicin.

21. A method according to claim 15, wherein said composition is in the form of an oily gel and contains from 40 to 97% by weight of peroxidized oil and from 0.010% to 0.08% by weight of pure capsaicin.

22. The method according to claim 15, wherein said composition is intended to prevent and/or to avoid eczematous manifestations, the formation of blisters or of vesicles as well as any erythematous action connected with the topical application on the skin of active principle having a skin-irritant character.

23. The method according to claim 15, wherein said active principle having a skin-irritant character is included in said composition.

* * * * *